US006924122B2

(12) United States Patent
Chien et al.

(10) Patent No.: US 6,924,122 B2
(45) Date of Patent: Aug. 2, 2005

(54) PROTEASE REGULATOR SCREENING ASSAY

(75) Inventors: David Y. Chien, Alamo, CA (US); Mark J. Selby, San Francisco, CA (US); Kevin Shoemaker, San Francisco, CA (US); Robert L. Warne, San Leandro, CA (US)

(73) Assignee: Chiron Corporation, Emeryville, CA (US)

( * ) Notice: Subject to any disclaimer, the term of this patent is extended or adjusted under 35 U.S.C. 154(b) by 158 days.

(21) Appl. No.: 10/225,390

(22) Filed: Aug. 20, 2002

(65) Prior Publication Data

US 2003/0113825 A1 Jun. 19, 2003

Related U.S. Application Data

(63) Continuation of application No. 08/997,055, filed on Oct. 17, 1997, now Pat. No. 6,436,666.
(60) Provisional application No. 60/028,817, filed on Oct. 17, 1996.

(51) Int. Cl.[7] .......................... A61K 38/24; C12P 21/06; C12N 15/00; C07K 1/00
(52) U.S. Cl. ................ 435/69.1; 435/172.3; 435/320.1; 530/350; 530/351; 530/399
(58) Field of Search ............................ 436/69.1, 172.3, 436/320.1; 530/350, 351, 399

(56) References Cited

U.S. PATENT DOCUMENTS

| 4,829,009 A | 5/1989 | Graves |
| 5,171,662 A | 12/1992 | Sharma |
| 5,227,489 A | 7/1993 | Law et al. |
| 5,292,652 A | 3/1994 | Dovey et al. |
| 5,347,076 A | 9/1994 | Pohlenz et al. |
| 5,386,013 A | 1/1995 | Lee et al. |
| 5,395,752 A | 3/1995 | Law et al. |
| 5,424,205 A | 6/1995 | Dovey et al. |
| 5,597,691 A | 1/1997 | Houghton et al. |

FOREIGN PATENT DOCUMENTS

| EP | 0 196056 A2 | 10/1986 |
| EP | 0 421109 A2 | 4/1991 |
| EP | 0 428000 A1 | 5/1991 |
| GB | 2276621 A | 10/1994 |
| WO | WO 95/02065 | 1/1995 |
| WO | WO 95/22985 | 8/1995 |
| WO | WO 96/35717 | 11/1996 |
| WO | WO 96/36702 | 11/1996 |

OTHER PUBLICATIONS

Rose and Craik, "Structure–Assisted Design of Nonpeptide Human Immunodeficiency Virus–1 Protease Inhibitors", Am. J. Respir. Crit. Care Med., 1994, S176–S182, vol. 150(6, pt2).
Heldsinger and Antonucci, "An HIV–1 Protease Sveening Assay Using a Non–infectious Proviral Clone", J. Virological Methods, 1994, 247–255, vol. 49.
Sudarsanam, et al., "An Approach to Computer–Aided Inhibitor Design: Application to Cathespin L", J. Computer–Aided Molecular Design, 1992, 223–233, vol. 6.
Holskin, et al., "A Continuous Flourescence–Based Assay of Human Cytomegalovirus Protease Using a Peptide Substrate", Analytical Biochemistry, 1995, 148–155, vol. 227.
Sato, et al., "A Simple and Rapid Method for Preliminary Evaluation of in Vivo Efficacy of Anti–HIV Compounds in Mice", Antiviral Research, 1995, 151–163, vol. 27.
Hellen, "Assay Methods for Retroviral Proteases", Methods in Enzymol., 1994, 46–58, vol. 241.
Sedlacek, et al., "A Rapid Screening Method for Biological Activity of Human Immunodeficiency Virus Proteinase Inhibitors by Using a Recombinant DNA–Derived Bacterial System", Analytical Biochemistry, 1993, 306–309, vol. 215.
Yu, et al., "Assay of HIV–1 Protease Activity by Use of Crude Preparations of Enzyme and Biotinylated Substrate," J. Virological Methods, 1995, 63–73, vol. 210(3).
Kakiuchi, et al., "Bacterial Expression and Analysis of Cleavage Activity of HCV Serine Proteinase Using Recombinant and synthetic Substrate", Biochemical and Biophysical Research Communications, 1995, 1059–1065, vol. 210(3).
Mori, et al., "Enzymatic Characterization of Purified Ns3 Serine Proteinase of Hepatitis C Virus Expressed in *Escherichia coli*", FEBS Letters, 1996, 37–42, vol. 378.
Steikuuhler, et al., Activity of Purified Hepatitis C Virus Protease NS3 on Peptide Substrates, Journal of Virology, Oct. 1996, 6694–6700.
Kim, et al., "Crystal Structure of the Hepatitis C Virus NS3 Protease Domain Complexed with a Synthetic NSA Cofactor Peptide", Cell. Oct. 18, 1996, 348–355, vol. 87.

*Primary Examiner*—Rodney P Swartz
(74) *Attorney, Agent, or Firm*—Lisa M. Hemmendinger; Charlene A. Launer; Alisa A. Harbin

(57) ABSTRACT

A polypeptide containing an anchor region, a protease recognition site, and a detectable signal region can be produced recombinantly and directly attached to a solid support. The polypeptide is useful for screening protease regulators, especially protease inhibitors.

11 Claims, 1 Drawing Sheet

PROTEASE REGULATOR SCREENING ASSAY

CROSS-REFERENCE TO RELATED APPLICATIONS

This application is a continuation of U.S. Ser. No. 08/997,055 filed Oct. 17, 1997, now U.S. Pat. No. 6,436,666 which claims the priority of U.S. Ser. No. 60/028,817 filed Oct. 17, 1996, each of which is incorporated herein by reference in its entirety.

FIELD OF THE INVENTION

The present invention is directed to polypeptides and methods useful for screening protease regulators such as inhibitors of hepatitis C virus (HCV) proteases.

BACKGROUND OF THE INVENTION

Protease activities have been implicated in many pathological processes of disease conditions, especially in viral infections. Protease regulators, especially protease inhibitors, are strongly desired for their potential therapeutic applications. For example, because HCV NS3 protease cleaves the non-structural HCV proteins which are necessary for HCV replication, the NS3 protease can be a target for the development of therapeutic agents against the HCV virus. Several methods are available in the field for screening protease inhibitors. However, there is a continuing need in the art to develop more effective methods and reagents for protease regulator screening.

SUMMARY OF THE INVENTION

It is an object of the present invention to provide a method for screening a compound capable of regulating protease activity.

It is another object of the invention to provide a polypeptide useful for screening test compounds for protease regulating activity.

It is yet another object of the invention to provide a method of forming a substrate for use in a screening assay for protease regulators.

These and other objects of the invention are provided by one or more of the embodiments provided below.

In one embodiment of the invention a method is provided for screening a compound capable of regulating protease activity. According to the method, a protease and a polypeptide are incubated in the presence and absence of a test compound. The polypeptide comprises an anchor region, a protease recognition site, and a detectable signal region. The anchor region is bound to a solid support. The protease recognition site comprises a) a protease cleavable peptide bond, and b) at least 3 amino acids on each side of the cleavable peptide bond. The signal region bound to the solid support is detected. An amount of the signal region bound to the solid support in the presence of the test compound which is greater or less than an amount detected in the absence of the test compound indicates that the test compound is capable of regulating protease activity.

In another embodiment of the invention a polypeptide consisting of a polyamino acid sequence is provided useful for screening test compounds for protease regulating activity. The polypeptide comprises an anchor region, a protease recognition site, and a detectable signal region. The anchor region is capable of binding to a solid support. The protease recognition site comprises a) a cleavable peptide bond, and b) at least 3 naturally adjacent amino acids on each side of the cleavable peptide bond.

In yet another embodiment a method is provided of forming a substrate for use in a screening assay for protease regulators. The method comprises the step of binding a polypeptide to a solid support via a protein-protein interaction. The $K_d$ of the protein-protein interaction is less than $10^{-8}$. The polypeptide comprises an anchor region, a protease recognition site, and a detectable signal region. The protease recognition site comprises a) a cleavable peptide bond, and b) at least 3 naturally adjacent amino acids on each side of the cleavable peptide bond. The polypeptide binds to the solid support via the anchor region.

The present invention provides the art with an effective and rapid method for screening protease regulators. The invention also provides polypeptides used in the method which can be easily produced recombinantly without any chemical modification. The method can be readily carried out in an automated format and is suitable for large scale drug screens.

DETAILED DESCRIPTION OF THE INVENTION

The present inventors have discovered a simple method of making substrates useful for screening protease regulators. A substrate is produced in a recombinant microorganism, isolated and purified, and directly attached to a solid support. Thus no in vitro chemical reactions are required to produce the assay substrate.

Figure 1A:
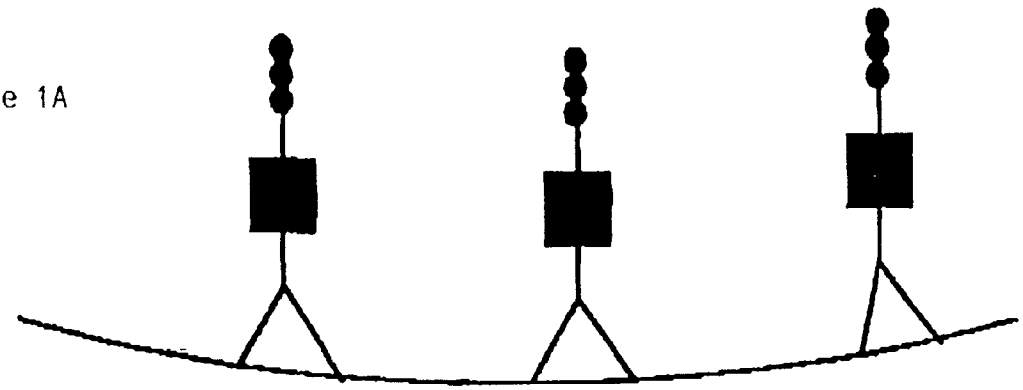
FIG. 1A is a schematic of the assay in the absence of protease cleavage. The polypeptide is anchored on a solid support. Y represents the anchor region, ■ represents the protease recognition site, and ●●●-represents the signal region.
Figure 1B:
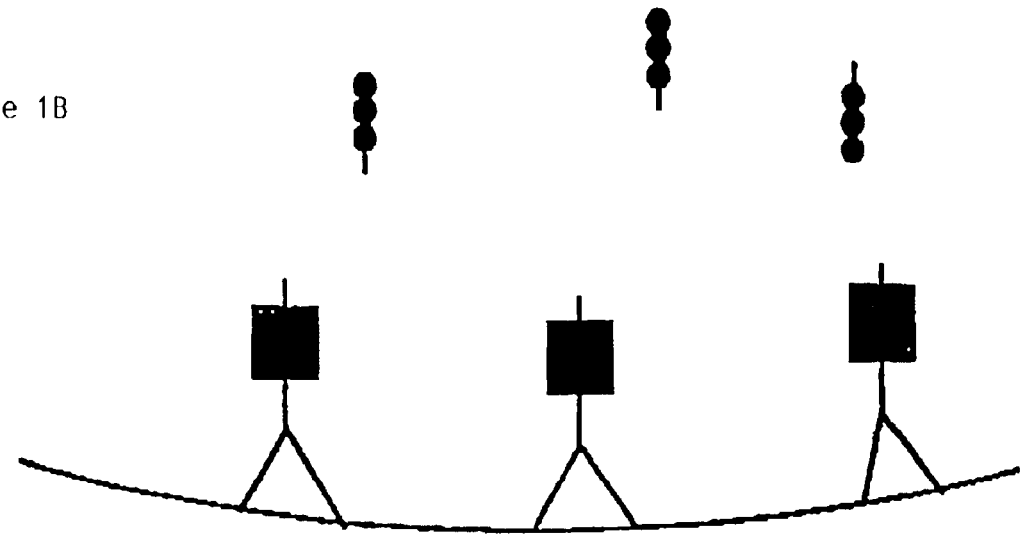
FIG. 1B is a schematic of the assay after protease cleavage. The signal region is released from the polypeptide and the solid support.

Polypeptides for the assay are solely comprised of amino acids. Thus they can be made recombinantly without subsequent chemical modification. They comprise an anchor region, a protease recognition site, and a detectable signal region (FIG. 1). The polypeptide can be made recombinantly using any means known in the art. For example, DNA sequences encoding each region can be ligated together and inserted into an expression vector via routine procedures of molecular biology (Molecular Cloning, A Laboratory Manual, Sambrook, Fritsch, Maniatis, Cold Spring Harbor Laboratory Press, 1989). Any expression vector available in the art, including prokaryotic and eukaryotic vectors, can be used to express the polypeptide of the present invention. One such vector is pEZZ18 (Pharmacia, N.J.). An expression vector encoding the polypeptide of the present invention can be used to transform host cells, either prokaryotic or eukaryotic host cells. The transformed host cells can either constitutively express or inducibly express the polypeptide of the present invention, depending on the promoter used in the expression vector.

Methods for purifying and/or isolating polypeptides made in expression systems are readily available in the art. For example, procedures for protein purification from *E. Coli* can be found at §17.37 of Molecular Cloning, A Laboratory Manual, second edition, Sambrook, Fritsch, Maniatis, Cold Spring Harbor Laboratory Press, 1989. Alternatively, the polypeptide can be made via non-recombinant methods, e.g., by chemical synthesis.

The anchor region of the polypeptide allows the polypeptide to be attached to a solid support during screening assays. It includes any peptide fragment that can be bound to a solid support via a protein-protein interaction. The interaction preferably has a $K_d$ of $10^{-8}$, $10^{-10}$, $10^{-12}$, or even $10^{-14}$. The $K_d$ of the protein-protein interaction should be less than $10^{-8}$.

Several peptide moieties are available in the art which may be used as anchor regions. For example, the anchor region can contain an epitope, an antibody binding region, or a protein capable of binding to another protein. The solid support can be coated with antibodies which bind to the epitope, or other proteins capable of specifically binding the anchor region. Numerous proteins or epitopes are suitable for use in the anchor region, e.g., protein A (Kronvall et al., Immunochemistry, 1970, 7: 124–127; Duhamel et al., J. Immunol. Methods, 1979, 31: 211–217), SOD polypeptide (Porstmann et al., J. Immunol. Methods, 1990, 127: 1–10), and S peptide (Kim et al., Protein Sci., 1993, 2: 348–356).

The anchor region can comprise any length from the minimum region required for protein binding to the entire protein. It can be at the N-terminal or C-terminal portion of the polypeptide, or in between. However, the anchor region must be positioned on the opposite side from the signal region with respect to the protease recognition site. The anchor region should also be positioned to minimize steric hindrance for the protease reaction. Steric hindrance if found, can be reduced by use of linker regions as discussed below.

The protease recognition site comprises a protease cleavable peptide bond flanked on both sides by at least 3 amino acids, preferably amino acids naturally adjacent to the protease cleavable peptide bond. In a more preferred embodiment, the peptide bond is flanked by at least 7 or 8 naturally adjacent amino acids on each side. Sequences of protease recognition sites for a variety of proteases are known in the art, e.g., the sequences of HCV protease cleavage sites NS5A/5B, NS4A/4B, and NS4B/5A (Grakoui et al., J Virol 1993 May; 67(5): 2832–2843). One or more copies of a single protease recognition site may be present in the polypeptide. They may be present in a series. In another embodiment, different cleavage sites are present in a series on the polypeptide. In yet another embodiment, polypeptides which contain different cleavage sites are attached to the same solid support.

The detectable signal region of the polypeptide is the moiety which is assayed to detect cleavage. The detectable signal region is positioned within the polypeptide on the opposite side of the protease recognition site from the anchor region. Thus, when the protease recognition site is cleaved by a protease, the detectable signal region is released from the solid support.

The detectable signal region is a substrate for a detecting reaction. It can comprise an epitope, an antibody binding region, an enzyme, a protein binding domain, or a nucleic acid binding domain. In a preferred embodiment, an epitope is used which comprises the amino acid sequence FLAG (SEQ ID NO:1) i.e., the FLAG tag. Other suitable epitopes comprise the amino acid sequence PLRQGGG (SEQ ID NO:2). An epitope containing a monotonous series of amino acids such as Glu or His, e.g., the 6-Histidine tag, can also be used in the present invention.

The detectable signal region can be detected directly, e.g., by labeled-monoclonal antibodies against epitope tags. In one embodiment, monoclonal antibodies are labeled with Europium and detected directly via time-resolved fluorometry. Time-resolved fluorometry is described in several articles, e.g., Hemmilä, I. Scand. J. Clin. Lab. Invest. 48: 389–400, 1988; Hemmilä et al., Anal. Biochem. 137:335–43; Lövgren et al., In: Alternative Immunoassays, Ed, Collins, W., John Wiley & Sons Ltd, Chichester, UK, pp. 203–217, 1985, all incorporated herein by reference. Alternatively, the primary antibodies can be conjugated to enzymes and detected by assaying for the enzymes.

The detectable signal region can also be detected indirectly, e.g., by labeled secondary antibodies which bind to primary monoclonal antibodies which bind to the epitope tags. Secondary antibodies can be labeled by means of enzymes conjugated to them, e.g., horse radish peroxidase (HRP) or alkaline phosphatase (AP).

A linker region may be used in the polypeptide. A linker region is a segment of the polypeptide located between any other domains, e.g., between the anchor region and the protease recognition site, or between the detectable signal region and the protease recognition site. A linker region comprises additional amino acids which provide flexibility to the polypeptide. These may be desirable to separate the domains of the polypeptide in order to allow access of the protease to the recognition site, or to present the recognition site for more efficient cleavage. Amino acid sequences suitable for use as a linker region are mostly neutral, e.g., Gly-Gly-Gly-Ser (SEQ ID NO:3). The size of a linker region can vary, depending on the particular polypeptide, from about 2 to about 25 amino acids, preferably from about 2 to about 9 amino acids, most preferably from about 3 to about 8 amino acids.

The solid support of the present invention facilitates high throughput screening. The solid support makes it possible to automate the screening assay without the need for excessive manipulation or transfer of the reaction. The solid support can be of any solid material, preferably plastic, such as polystyrene or polycarbonate. Most preferably it is a multi-compartment vessel for screening multiple candidates at once. The solid support can also be in the form of paramagnetic particles (PMPs), latex particles, paramagnetic latex particles, membranes, polystyrene microbeads, and glass beads.

The polypeptide can be used to screen for protease inhibitors as well as protease activators. The proteases for which a regulator is screened include but are not limited to cellular proteases and viral proteases, e.g., HCV proteases and HIV proteases. Protease inhibitors can be used therapeutically to inhibit viral infection. Protease activators can be useful for enhancing cellular signal transduction associated with proteases. In particular, hepatitis C virus (HCV) has been isolated and characterized. See, e.g. EP-318,216B, EP-388232A, and EP-398748. The HCV proteases are also known. See, e.g., U.S. Pat. Nos. 5,371,017; 5,597,691; and 5,585,258. Test compounds or candidate protease regulators include libraries of molecules, preferably combinatorial libraries, containing, e.g., small organic chemicals, peptides, or oligonucleotides.

To perform a screening assay, a protease and the polypeptide of the present invention are incubated in the presence and absence of a test compound. The polypeptide can be bound to a solid support either before or after the incubation. Such incubation is carried out under conditions where the protease can cleave its substrate. HCV NS3 protease requires a co-factor, peptide 4A, in order to cleave the NS4B/5A site in HCV. HCV proteases and their co-factors are described in Steinkühler et al., J. of Virology, pp 6694–6700, 1996; Kim et al., Cell, Vol. 87, pp 343–355, 1996; and WO96/36702, all incorporated herein by reference. Conditions for other HCV protease cleavages are well characterized in the art. HCV cleavage conditions are exemplified in the examples described below. Cleavage sites and conditions for other proteases are also known. See, e.g., U.S. Pat. No. 5,434,074.

After incubation, the cleaved portion of the polypeptide is washed away and the polypeptide bound to the solid support is subjected to a detecting reaction which determines the amount, presence, or absence of the signal region bound to the solid support. Conversely the amount of signal region which is washed away can be determined. Detection of a greater amount of the signal region bound to the solid support in the presence of the test compound than in the absence of the test compound indicates that the test compound is capable of inhibiting protease activity. Alternatively, detection of a smaller amount of the signal region bound to the solid support in the presence of the test compound than in the absence of the test compound indicates that the test compound is capable of activating or enhancing protease activity.

The sensitivity of the screening assay is based on several factors including the amount of the protease used and the sensitivity of the detection of the signal region. In order to maximize the sensitivity of the assay for detecting inhibitors, the amount of the protease used should be adjusted to give a very low reading of the signal region bound to the solid support in the absence of a test compound, i.e., close to 100% cleavage by the protease used. Conversely, for detecting enhancers a very low amount of cleavage is desired in the absence of a test compound.

The following examples are provided for exemplification purposes only and are not intended to limit the scope of the invention which has been described in broad terms above.

EXAMPLE 1

The HCV Protease Inhibitor Screening Assay Using NS5A/5B As Cleavage Site Expression Construct and its Encoded Polypeptide An expression construct of the present invention was made using standard techniques available in the art. A commercially available vector containing Protein A epitope, i.e., pEZZ18 (Pharmacia, N.J.) was used as the starting point to build the expression construct.

A fragment encoding HCV NS5 peptide protease target site was inserted in frame into the polylinker region of pEZZ18 so that it is connected at the C-terminal region of Protein A. The NS5 peptide protease target site includes the NS5A and NS5B cleavage site, i.e., amino acids 2420 and 2421, 7 amino acids at the N-terminal side of the cleavage site, and 8 amino acids at the C-terminal side of the cleavage site.

Another sequence fragment encoding the FLAG tag was inserted in frame at the C-terminal end of the NS5 peptide protease target site. The sequence fragment encodes three FLAG tags alternately spaced with two 4-Glycine spacers.

The resulting expression plasmid construct was expressed in bacteria. Purification of the expression product was carried out via a routine procedure. The overnight bacterial culture was spun down. The supernatant was passed through a 0.45 micron filter and subsequently placed on to an Ig-Sepharose column. The column was eluted with 0.5M Glycine at pH 3.5. The eluted protein was neutralized, concentrated, and desalted using a Centricon-10 spin column.

Coating the Plates

Microwell plates containing 96 wells were prepared by coating the wells with IgG. Then the plates were dried. The purified protein NS5 was incubated with the dry plates for 1 hour at 37° C. to allow binding of the Protein A region of the protein to the IgG in the microwells.

The Protease

Protease was prepared by elution from a nickel column. Various concentrations of HCV protease were prepared. The protease was incubated with and without a known protease inhibitor, DCIC (di-chloro-iso-coumarin). The incubation was for 1 hour at room temperature. Subsequently the protease was transferred to the coated plates. The incubation was continued overnight at room temperature and then the plate was washed.

The Detection

Diluted monoclonal anti-FLAG mouse antibodies (available from Kodak) were added to the HCV protease treated plates and incubated with the plates for 1 hour at 37° C. The plates were subsequently washed and incubated with affinity purified goat anti-mouse-HRP (horse radish peroxidase) conjugates for 1 hour at 37° C. Then the plates were washed, and incubated with a developer such as o-phenylenediamine dihydrochloride (OPD). The optical density (OD) was determined at 492 and 620 nm settings.

Experimental Design:

a) Different protease preparations were tested at different concentrations for their protease activity in the absence of a protease inhibitor.

TABLE 1

| 50 ng substrate\ well plate | OD of the reaction product | | | |
|---|---|---|---|---|
| | 1:20 protease dilution | 1:50 protease dilution | 1:100 protease dilution | protease activity |
| protease 1 | 0.036 | 0.041 | 0.037 | + |
| protease 2 | 0.091 | 0.131 | 0.201 | + |
| protease 3 | 0.284 | 0.265 | 0.263 | ± |
| protease 4 (negative control) | 0.263 | 0.263 | 0.255 | − |
| protease 5 (negative control) | 0.245 | 0.234 | 0.242 | − |
| protease 6 (negative control) | 0.266 | 0.280 | 0.281 | − |
| substrate | 0.013 | 0.009 | 0.010 | − |
| PBS | 0.008 | 0.005 | 0.001 | − |

TABLE 2

| 200 ng substrate\ well plate | OD of the reaction product | | | |
|---|---|---|---|---|
| | 1:20 protease dilution | 1:50 protease dilution | 1:100 protease dilution | protease activity |
| protease 1 | 0.075 | 0.069 | 0.091 | + |
| protease 2 | 0.281 | 0.412 | 0.497 | + |
| protease 3 | 0.770 | 0.930 | 0.769 | ± |
| protease 4 (negative control) | 0.822 | 0.919 | 0.780 | − |
| protease 5 (negative control) | 0.833 | 0.870 | 0.828 | − |
| protease 6 (negative control) | 0.847 | 0.813 | 0.788 | − |
| substrate | 0.011 | 0.018 | 0.010 | |
| PBS | 0.006 | 0.006 | 0.007 | | protease 1: Ni-13 (F21) 20 μM, preparation made at Chiron.
protease 2: HCV P Feb. 23, 1996, preparation made at Chiron.
protease 3: NS3 4A (F1), preparation made at Chiron.
protease 4: NS3 4A mnt, (3), mutant protease, preparation made at Chiron.
protease 5: NS3 4A mnt, (2), mutant protease, preparation made at Chiron.
protease 6: CA3, mutant protease, preparation made at Chiron
substrate: pro A-NS5, 1xPBS, polypeptide substrate of HCV protease The results as shown in tables 1 and 2 demonstrate that protease preparations 1 and 2 are good candidates to be used for the screening assay. For the following experiments, protease preparation 1 was used.

b) Determination of the incubation time and the specificity of the screening assay.

TABLE 3

Control Setups

|  | substrate (pro A-NS5) | protease | protease inhibitor (DCIC) | monoclonal anti-FLAG mouse antibody | goat anti-mouse conjugate |
|---|---|---|---|---|---|
| control 1 | + | − (PBS) | − (PBS) | − (PBS) | + |
| control 2 | + | − (PBS) | − (PBS) | + | + |
| control 3 | + | + | − (PBS) | + | + |
| control 4 | + | + | + | + | + |

TABLE 4

Incubation time: substrate (proA-NS5) and protease was incubated overnight

| | OD (pro A-NS5 10 μg/ml) | | | | OD (proA-NS5 2 μg/ml) | | | |
|---|---|---|---|---|---|---|---|---|
| | pro. 0 | pro. 1:100D | pro. 1:200D | pro. 1:500D | pro. 0 | pro. 1:100D | pro. 1:200D | pro. 1:500D |
| control 1 | 0.042 | N\A | N\A | N\A | 0.034 | N\A | N\A | N\A |
| control 2 | 0.913 | N\A | N\A | N\A | 0.668 | N\A | N\A | N\A |
| control 3 | N\A | 0.260 | 0.249 | 0.364 | N\A | 0.198 | 0.182 | 0.311 |
| control 4 | N\A | 0.899 | 0.998 | 0.887 | N\A | 0.449 | 0.467 | 0.328 |

TABLE 5

Incubation time: substrate (proA-NS5) and protease were incubated for 2 hours

| | OD (pro A-NS5 10 μg/ml) | | | | OD (proA-NS5 2 μg/ml) | | | |
|---|---|---|---|---|---|---|---|---|
| | pro. 0 | pro. 1:100D | pro. 1:200D | pro. 1:500D | pro. 0 | pro. 1:100D | pro. 1:200D | pro. 1:500D |
| control 1 | 0.004 | N\A | N\A | N\A | 0.010 | N\A | N\A | N\A |
| control 2 | 1.209 | N\A | N\A | N\A | 0.770 | N\A | N\A | N\A |
| control 3 | N\A | 0.667 | 0.677 | 1.488 | N\A | 0.606 | 0.352 | 0.835 |
| control 4 | N\A | 1.137 | 1.235 | 0.503 | N\A | 0.627 | 0.631 | 0.545 |

TABLE 6

Incubation time: preincubation of protease, protease substrate, and protease inhibitor overnight

| | OD (pro A-NS5 10 μg/ml) | | | |
|---|---|---|---|---|
| | protease 0 | protease 1:100D | protease 1:200D | protease 1:500D |
| control 1 | 0.003 | N\A | N\A | N\A |
| control 2 | 1.136 | N\A | N\A | N\A |
| control 3 | N\A | 0.289 | 0.247 | 0.315 |
| control 4 | N\A | 1.578 | 1.458 | 1.083 |

The results as shown in Tables 4–6 demonostrate that the screening assays is specific protease cleavage. The data also demonstrate the dependence of the assay on incubation time of the substrate and the protease.

c) Testing pools 11896 and 11890 of Chiron's compound library for protease inhibiting activity.

TABLE 7

Protease, protease substrate, and protease inhibitor were preincubated overnight

| | Exp. 1 | Exp. 2 | [OD(control 4)/OD (test inhibitor)] = I/E | [OD(test inhibitor-OD (reference inhibitor*)]/OD(test inhibitor) = I % |
|---|---|---|---|---|
| control 1 | 0.021 | 0.066 | | |
| control 2 | 1.234 | 0.930 | | |
| control 3 | 0.354 | 0.227 | | |
| control 4 | 1.235 | 0.768 | 1.235/0.354 = 3.5x<br>0.768/0.227 = 3.4x | |
| control 4 with 11896 as the inhibitor | 0.471 | 0.306 | 1.235/0.471 = 2.6x<br>0.768/0.306 = 2.51x | (0.471 − 0.354)/<br>0.471 = 25.7%<br>(0.306 − 0.227)/<br>(1:100D)<br>0.306 = 26.2% |
| control 4 with 11890 as the inhibitor (1:100) | 0.387 | 0.294 | 1.235/0.387 = 3.19x<br>0.768/0.294 = 2.61x | (0.387 − 0.354)/<br>0.387 = 9%<br>(0.294 − 0.227)/<br>0.294 = 23.4% |

*reference inhibitor: protease inhibitor DCIC which represents 100% inhibition.

EXAMPLE 2

The HCV Protease Inhibitor Screening Assay Using NS4B/5A Cleavage Site a) Experimental Procedure Materials:

Plate: Human IgG coated on HB COSTAR plate, 200 ng/well

Conjugate: Affinity purified goat anti-mouse (H+L)-HRP (Fab)2, (1:5K)

Conjugate Diluent: Ortho conjugate diluent

Protein A-NS5 construct: 10 µg/ml in 1×PBS

Mouse monoclonal anti-FLAG M2 (IBI, IB13010/6j0612): 1:200d in conjugate diluent Enzyme Stock Buffer: 20 mM Tris, 50% glycerol, 150 mM NaCl, 0.2% Ethyglucoside, (5 mM DTT)

The protease: Ni-13 (F21) diluted 1:300 in the enzyme stock buffer

The protease inhibitor: diluted to 1 mM in the enzyme stock buffer

The pharmaceutical protease inhibitor: diluted to 1 µM in the enzyme stock buffer A substrate polypeptide was prepared having an anchor region (protein A), a linker, two protease target sites of NS4B/5A, another linker, and a FLAG epitope tag. The target polypeptide was expressed in sufficient quantities to conduct the assay.

The substrate polypeptide, (10 µg/well) in 200 µl was added to a human IgG coated plate and incubated for one hour. The plate was washed five times with wash buffer. The inhibitor, if any, was pre-incubated (diluted to 1 uM) with HCV protease, NS4A (0.2 uM) for one hour at room temperature. Peptide 4A, a co-factor of the NS3 HCV protease was added in different concentrations to all wells containing the protease mixture (20X concentration is 4 µM). The above mixture was transferred to the plate coated with IgG-4B/5A complex and incubated overnight at room temperature (about 20° C.–25° C.). The final concentration of the NS4A in each well was 4 µM. The plate was washed five times in wash buffer. Mouse anti-FLAG monoclonal antibody in the amount of 200 µl (1:200d from stock solution) was added to the designated wells and incubated one hour at 37° C. The plate was washed five times with wash buffer. Affinity purified goat anti-mouse (H+L)-HRP (Fab')$_2$ conjugate (1:5000d) in the amount of 200 µl was added to all the reaction wells except the blank well and incubated one hour at 37° C. The plate was washed five times with wash buffer. Then the plate was developed with OPD substrate for 30 minutes at room temperature. The plate was read with a microtiter plate reader at 490/620 nm.

b) Results

TABLE 8

Substrate 4B/5A: 10 µg/well

| | OD of the reaction product | | |
|---|---|---|---|
| | no peptide 4A | 10X peptide 4A | 20X peptide 4A |
| 1X PBS | 0.015 | 0.034 | 0.016 |
| substrate only | 1.645/1.626 | 1.643/1.570 | 1.403/1.453 |
| substrate + protease | 1.224/1.207 | 0.706/0.668 | 0.541/0.539 |
| substrate + protease + DCIC inhibitor (1 µM) | 1.769/1.686 | 1.729/1.715 | 1.584/1.690 |

TABLE 9

Substrate 4B/5A: 5 µg/well

| | OD of the reaction product | | |
|---|---|---|---|
| | no peptide 4A | 10X peptide 4A | 20X peptide 4A |
| 1X PBS | 0.505 | 0.43 | 0.039 |
| substrate only | 1.357/1.312 | 1.292/1.187 | 1.252/1.207 |
| substrate + protease | 1.013/0.970 | 0.564/0.603 | 0.538/0.543 |
| substrate + protease + DCIC inhibitor (1 µM) | 1.400/1.491 | 1.435/1.328 | 1.374/1.373 |

These data demonstrates the operability of the screening assay using HCV NS4B/5A protease cleavage site with co-factor peptide 4A.

EXAMPLE 3

Using NS5A/5B as Substrate to Screen HCV Protease Inhibitor Candidates a) Experimental Procedure A target polypeptide was prepared having an anchor region, a linker region, a protease target site of HCV NS5A/5B, another linker region, and a FLAG epitope tag region. The experiment was designed as in Example 2.

b) Results

TABLE 10 control setup: since some protease inhibitor candidates were not water soluble and were dissolved in DMSO, controls for DMSO were added.

| | pro A-NS5 | protease | protease inhibitor (DCIC) | monoclonal anti-FLAG mouse antibody | goat anti-mouse conjugate | OD w/ DMSO 1 µl | ODw/o DMSO |
|---|---|---|---|---|---|---|---|
| control 1 | + | − (PBS) | − (PBS) | − (PBS) | + | N\A | 0.010 |
| control 2 | + | − (PBS) | − (PBS) | + | + | N\A | 2.602 |
| control 3 | + | + | − (PBS) | + | + | 0.702 | 0.680 |
| control 4 | + | + | + | + | + | 2.596 | 2.915 |

TABLE 11

Testing different protease inhibitor pools:

| Pharmaceutical Protease Inhibitor Pools (1 µM) | OD w/DMSO | Mean of OD w/DMSO |
|---|---|---|
| Drug 21509 | 0.765 | 0.767 |
| | 0.769 | |
| Drug 11888 | 2.141 | 2.099 |
| | 2.057 | |
| Drug 11892 | 1.786 | 1.923 |
| | 2.060 | |
| Drug 12427 | 1.042 | 1.034 |
| | 1.027 | |
| Drug 12425 | 0.865 | 0.848 |
| | 0.831 | |
| Drug 12447 | 1.558 | 1.537 |
| | 1.516 | |
| Drug 13318 | 0.780 | 0.830 |
| | 0.880 | |

TABLE 11-continued

Testing different protease inhibitor pools:

| Pharmaceutical Protease Inhibitor Pools (1 μM) | OD w/DMSO | Mean of OD w/DMSO |
|---|---|---|
| Drug 6769 | 1.037 | 1.087 |
| | 1.138 | |
| Drug 6768 | 1.080 | 1.072 |
| | 1.064 | |
| Drug 6763 | 1.209 | 1.145 |
| | 1.082 | |
| Drug 6760 | 1.136 | 1.153 |
| | 1.171 | |
| Drug 6757 | 1.421 | 1.366 |
| | 1.311 | |
| Drug 6756 | 1.313 | 1.301 |
| | 1.290 | |

TABLE 12

| protease inhibitor pool | library (Chiron) | number of compounds/ library pool | inhibition of protease activity % |
|---|---|---|---|
| A 1 μM | benzodiazopine | 500 | 23 |
| B 1 μM | benzodiazopine | 500 | 35 |
| C 1 μM | benzodiazopine | 500 | 19 |
| D 1 μM | benzodiazopine | 500 | 20 |
| E 0.5 μM | dihydro-isoquinolone I | 40 | 16 |
| F 1 μM | benzodiazopine | 500 | 23 |
| G 1 μM | benzodiazopine | 500 | 32 |
| H 1 μM | dihydro-pyridone | 27 | 64 |
| I 1 μM | dihydro-isoquinolone II | 40 | 7 |
| J 1 μM | beta-lactam V | 100 | 3 |
| K 1 μM | Azepinone | 40 | 44 |
| L 1 μM | dihydro-isoquinolone II | 40 | 7 |
| M 1 μM | dihydro-pyridone | 27 | 73 |

EXAMPLE 4
Using a Short Incubation Time and NS5A/5B as a Substrate to Screen HCV Protease Inhibitors
a) Experimental Procedure A target polypeptide was prepared having an anchor region (protein A) molecule, a linker, a protease target site of HCV NS5A/5B, another linker, and a FLAG epitope tag region. The target polypeptide was expressed in sufficient quantities to conduct the assay The inhibitor was pre-incubated (diluted to 1 μM) with HCV protease (0.2 μM) for 1 hour at room temperature. A solution of NS5A/5B substrate (20 μg/well) was added to the pre-incubated protease and protease inhibitor mixture, and the total mixture was incubated for 15 minutes. The mixture was transferred to a human IgG coated plate and incubated for 1 hour at 37° C. The plate was washed five times with wash buffer.

Two hundred microliter of mouse anti-FLAG monoclonal antibody (1:200d from stock solution) was added to the designated wells and incubated for 1 hour at 37° C. The plate was washed five times with wash buffer. Affinity purified goat anti-mouse (H+L)-HRPO (Fab')$_2$ conjugate (1:5000d) in the amount of 200 μl was added to all the reaction wells except the blank well and incubate 1 hour at 37° C. The plate was washed five times with wash buffer. The plate was developed with OPD substrate for 30 minutes at room temperature. The plate was read with a microtiter plate reader at 490/620 nm.

b) Results

TABLE 13

Control setup

| | pro A-NS5 | pro. | pro. in-hibitor (DCIC) | mono. anti-FLAG mouse anti-body | goat anti-mouse conju-gate | 15 minutes preincu-bation | 1 hour preincu-bation |
|---|---|---|---|---|---|---|---|
| control 1 | + | − (PBS) | − (PBS) | − (PBS) | + | 0.007/ 0.018 | 0.000/ 0.016 |
| control 2 | + | − (PBS) | − (PBS) | + | + | 1.383/ 1.557 | 2.353/ 2.002 |
| control 3 | + | + | − (PBS) | + | + | 0.794/ 0.701 | 0.580/ 0.628 |
| control 4 | + | + | + | + | + | 1.563/ 1.590 | 1.991/ 2.152 |

TABLE 14

Testing different protease inhibitor pools with different preincubation time:

| pro. inhibitor pools (Chiron) | OD (1 hour* preincubation) | inhibition % (per μM) | OD (15 minutes* preincubation) | inhibition % (per μM) |
|---|---|---|---|---|
| H (300 μM) | 0.640/0.867 | 20 | 1.083/1.176 | 46 |
| E (200 μM) | 0.614/0.598 | 0 | 0.912/0.924 | 20 |
| N (200 μM) | 0.650/0.605 | 3 | 0.849/0.950 | 4 |
| O (200 μM) | 0.570/0.694 | 4 | 0.605/0.670 | 0 |
| P (200 μM) | 1.367/1.258 | 54 | 1.491/1.280 | 77 |
| Q (200 μM) | 1.393/1.230 | 54 | 0.788/1.237 | 26 |
| J (1 mM) | 0.642/0.613 | 4 | 0.796/0.960 | 16 |
| R (2 mM) | 0.598/0.613 | 0 | 0.771/0.869 | 9 |
| S (2 mM) | 0.550/0.667 | 0 | 0.686/0.817 | 0 |
| T (2 mM) | 0.685/0.594 | 5 | 0.957/0.884 | 21 |
| U (2 mM) | 0.620/0.623 | 3 | 0.881/0.982 | 22 |
| V (200 μM) | 0.645/0.596 | 3 | 0.912/1.061 | 29 |

*two duplicates are shown

This experiment demonstrates that with more protease inhibition is observed at 15 minutes preincubation than with 1 hour preincubation.

EXAMPLE 5
Tandem Assay

The tandem assay is performed with two substrate polypeptides: (1) a polypeptide having both an HCV NS4B/5A site and an HCV NS4A/4B site and (2) a polypeptide having an HCV NS5A/5B site.

The first substrate polypeptide includes a protein A anchor region, a linker region, a NS4B/5A target site, a NS4A/4B target site, another linker, and a flag epitope. The second target polypeptide includes a SOD anchor region, a linker region, a NS5A/5B site, another linker region, and a PLRQGGG (SEQ ID NO:1) epitope.

The first target polypeptide was incubated with paramagnetic particles (PMP) coated with human IgG at 37° C. for 18 minutes to form PMP-1. The second target polypeptide was incubated with PMP coated with anti-SOD monoclonal antibodies at 37° C. for 18 minutes to form PMP-2.

NS3 HCV protease and 4A peptide in the presence and absence of a protease inhibitor were preincubated for an hour at room temperature and were added into a mixture of PMP-1 bound with first target polypeptide containing 4A/4B and 4B/5A (30 µg/assay) and PMP-2 bound with second target polypeptide containing 5A/5B (30 µg/assay). The total reaction mixture was incubated at room temperature for 18 minutes and then washed 5 times with assay wash buffer. Subsequently, murine monoclonal anti-FLAG epitope antibody conjugated to 2',6'-Dimethyl-4'-(N-succinimidyloxycarboxnyl)Phenyl 10-3'-Sulfopropyl)-acridinium-9-carboxylate (NSP-DMAE-NHS) (100 µl of 1:50000 dilution) and murine monoclonal anti-PLRQGGG epitope antibody conjugated to (2',6'-Dimethyl-4-N-succinimidyloxycarboxnyl)phenyl 5-Methyl-benz[b]acridinium-12-carboxylate Fluorosulfonate (LEAE-NHS), (100 µl of 1:50000 dilution) were incubated with the reaction mixture for 18 minutes at 37° C. The reaction mixture was then washed five times followed by addition of hydrogen peroxide and NaOH. The relative light units (RLU) were read on Dual Wavelengths Photo Multiplier System made by Ciba Coming Diagnostic, Inc., Walpole, MA. DMAE is detectable at 450 nm wavelength and LEAE is detectable at 600 nm wavelength.

EXAMPLE 6

Screening Assay Using Monoclonal Antibodies Directly Labeled With $Eu^{3+}$ and Time-Resolved Fluorometry Detection Technology.

Reagents:

Reaction Buffer: 50 mM Hepes (pH 7.6), 3 mM $MgCl_2$, 50% glycerol (v/v), 1 mM DTT (added fresh), 0.1% BSA (added fresh).

Delfia Wash Buffer: 5 mM Tris (pH 7.6), 0.01% Tween-20, 150 mM NaCl, 1.5 mM NaAzide.

Delfia Assay Buffer: purchased from Wallac, cat# 138-022-91.

Delfia Enhancement Solution: purchased form Wallac, cat#1244-105.

Protease: Ni-Large#18 prep from Mike Chin at Chiron. This construct has a free N-terminus and a C-terminal 6XHIS tag. Stock concentration is 359 µM. It was diluted 1:16,320 in the reaction buffer and 180 µl of which was added into a 200 µl reaction to reach a final protease concentration of 20 nM.

NS4A peptide: purchased from CPR, cat#CIS 2812, lot#CEO 412. The sequence of the 4A peptide is KKGSVVIVGRIVLSGKPAIIPKK-OH. The stock concentration is 12.5 mM in DMSO and 10 mM DTT. It was diluted 1:11,360 into diluted protease solution. The final concentration of 4A peptide was 1 µM.

Substrate: protein A-G-G-G-G-7aa-NS4B/5A cleavage site-8aa-FLAG-G-FLAG-G-FLAG. The concentration of the stock solution is 724 µM. It was diluted 1:3620 in reaction buffer and 20 µl of which was added into 200 µl reaction to reach a final concentration of 20 nM.

$Eu^{3+}$-anti-FLAG MoAb: purchased from Sigma via Kodak, cat#IB 13026, lot#710413. $Eu^{3+}$ labeling reagent was purchased from Wallac, cat# 1244301. The concentration of the stock solution is 10 µM. It was diluted 1:1,175 in Delfia assay buffer and 200 µl of which was added into each reaction well.

IgG: purchased from Sigma, cat#I-2511, lot#027H4804. The concentration of the stock solution is 4.8 mg/ml. It was stored in small aliquots at −70° C. It was thawed once before using in the reaction. The stock solution was diluted 1:320 in PBS and 200 µl of which was added into each reaction well to reach a final concentration of 15 µg/ml.

Plates: Immulon-4 flat bottom plate was used for IgG coating. It was purchased from Fisher, Dynatech cat#0110103855. For initial reaction, Falcon 96-well U-bottom plate was used. It was purchased from Fisher.

Plate Sealer: soft plastic seals for 96-well plates, cat#320060, purchased from Fisher.

Procedure

Immulon-4 plates were sealed and incubated with IgG (200 µl of 15 µg/ml in PBS) for 2 hours at 37° C. The plates were then washed 5 times with 200 µl of Delfia wash buffer and blocked by incubating with 200 µl of low detergent BLOTTO for 1 hour at 37° C. Alternatively, the plates were blocked overnight at 4° C.

A mixture of protease, 4A peptide, and the reaction buffer was prepared by adding 21.4 µl of protease stock and 30.8 µl of 4A peptide stock to 350 ml of reaction buffer. The mixture in the amount of 180 µl was added into an assay plate. The reaction buffer in the same amount was also added into the assay plate as a negative control. The assay plate was sealed and stayed at room temperature for 1 hour.

A substrate solution was prepared by adding 13.8 µl of the stock into 50 ml of the reaction buffer. The substrate solution in the amount of 20 µl was added into each well of the assay plate containing the protease and 4A peptide. The plate was once again sealed and kept at room temperature for 1 hour. Subsequently, an aliquot (200 µl) of the reaction mixture in each well of the assay plate was transferred into the wells of IgG coated Immulon-4 plate. The IgG coated plate containing the reaction mixture of the assay plate was sealed and kept at 37° C. for 1 hour. Then it was washed five times with 200 µl Delfia wash buffer.

Subsequently, a solution of $Eu^{3+}$-anti-FLAG MoAb was prepared by addition of 228 µl $Eu^{3+}$-anti-FLAG MoAb into 400 ml Delfia assay buffer. The solution was then passed through a 0.45 µm filter and 200 µl of which was added into each well of the IgG coated plate. The plate was once again sealed, kept at 37° C. for 1 hour, and washed 5 times with 200 µl Delfia wash buffer. Then the plate with Delfia enhancement solution (200 µl) added into each well was gently shaken for 10 minutes and was ready for $Eu^{3+}$ reading.

Results

TABLE 15

| | | | Results | | |
|---|---|---|---|---|---|
| Substrate | Protease | NS4A peptide | DMSO | protease inhibitor (Chiron ID 34602.2) | $Eu^{3+}$ counts |
| + | | | 0.50% | | 1,307,260 |
| + | | | 2.50% | | 1,256,640 |
| + | + | | 0.50% | | 1,103,418 |
| + | + | | 2.50% | | 1,111,651 |
| + | + | + | 0.50% | | 291,779 |
| + | + | + | 2.50% | | 369,729 |
| + | + | + | | 3 µM | 540,263 |
| + | + | + | | 15 µM | 869,825 |

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

Synopsis of the Invention

1. A method for screening a compound capable of regulating protease activity comprising the steps of:
    incubating in the presence and absence of a test compound, a protease and a polypeptide wherein the polypeptide comprises an anchor region, a protease recognition site, and a detectable signal region, wherein the anchor region is bound to a solid support and the protease recognition site comprises a) a protease cleavable peptide bond, and b) at least 3 naturally adjacent amino acids on each side of the cleavable peptide bond, detecting the signal region bound to the solid support, wherein detecting an amount of the signal region bound to the solid support in the presence of the test compound which is greater or smaller than an amount detected in the absence of the test compound indicates that the test compound is capable of regulating protease activity.

2. The method of item 1 wherein the anchor region specifically binds to an antibody.

3. The method of item 2 wherein the anchor region comprises protein A.

4. The method of item 1 wherein the protease recognition site is a hepatitis C virus (HCV) protease recognition site which is selected from the group consisting of 4A/4B, 4B/5A, 5A/5B, and serial combinations thereof.

5. The method of item 1 wherein the signal region comprises an epitope.

6. The method of item 5 wherein the epitope comprises the amino acid sequence FLAG (SEQ ID NO:1).

7. The method of item 1 wherein the polypeptide further comprises a linker region between the anchor region and the protease recognition site.

8. The method of item 1 wherein the protease recognition site comprises a) a protease cleavable peptide bond, and b) at least 3 naturally adjacent amino acids on each side of the cleavage peptide bond.

9. The method of item 1 wherein the anchor region specifically binds to an antibody, the protease recognition site is a HCV protease recognition site which is selected from the group consisting of 4A/4B, 4B/5A, 5A/5B, and serial combinations thereof, and the signal region comprises an epitope.

10. The method of item 9 wherein the anchor region comprises protein A and the epitope comprises the amino acid sequence FLAG (SEQ ID NO:1).

11. The method of item 10 further comprising a linker region between the anchor region and the protease recognition site.

12. A polypeptide consisting of a polyamino acid sequence, said polypeptide being useful for screening test compounds for protease regulating activity, said polypetide comprising an anchor region, a protease recognition site, and a detectable signal region, wherein the anchor region is capable of binding to a solid support, the protease recognition site comprises a) a cleavable peptide bond, and b) at least 3 naturally adjacent amino acids on each side of the cleavable peptide bond.

13. The polypeptide of item 12, wherein the detectable signal region comprises an epitope.

14. The polypeptide of item 12, wherein the anchor region specifically binds to an antibody.

15. The polypeptide of item 14, wherein the anchor region comprises protein A.

16. The polypeptide of item 12, wherein the protease recognition site is a HCV protease recognition site and is selected from the group consisting of 4A/4B, 4B/5A, 5A/5B, and serial combinations thereof 17. The polypeptide of item 12, wherein the detectable signal region comprises the amino acid sequence FLAG (SEQ ID NO:1).

18. The polypeptide of item 12, wherein the anchor region comprises protein A, the protease recognition site is a HCV protease recognition site selected from the group consisting of 4A/4B, 4B/5A, 5A/5B, and serial combinations thereof, and the epitope comprises the amino acid sequence FLAG (SEQ ID NO:1).

19. An expression vector comprising a DNA sequence encoding the polypeptide of item 12.

20. The vector of item 19 wherein the expression vector is a prokaryotic expression vector.

21. A host cell transformed with the vector of item 20.

22. The method of item 11 wherein detection of an amount of the signal region on the solid support in the presence of the test compound which is greater than an amount detected in the absence of the test compound indicates that the test compound is capable of inhibiting protease activity.

23. The method of item 11 wherein detection of an amount of the signal region on the solid support in the presence of the test compound which is less than an amount detected in the absence of the test compound indicates that the test compound is capable of enhancing protease activity.

24. A method of forming a substrate for use in a screening assay for protease regulators comprising the steps of:

binding a polypeptide consisting of a polyamino acid sequence to a solid support via a protein-protein interaction, wherein $K_d$ of the protein-protein interaction is no more than $10^{-8}$, wherein the polypeptide comprises an anchor region, a protease recognition site, and a detectable signal region, wherein the protease recognition site comprises a) a cleavable peptide bond, and b) at least 3 naturally adjacent amino acids on each side of the cleavable peptide bond, and wherein the polypeptide binds to the solid support via the anchor region.

25. The method of item 24, wherein the detectable signal region contains an epitope.

26. The polypeptide of item 12 which is bound to a solid support.

27. A method for screening a compound capable of regulating protease activity comprising the steps of:

expressing the polypeptide of item 11, 12, 13, 14, 15, or 16 in a host, isolating the polypeptide, binding the polypeptide to a solid support via a protein-protein interaction, incubating the polypeptide with a protease in the presence and absence of a test compound, detecting the signal region bound to the solid support, wherein detecting an amount of the signal region on the solid support in the presence of the test compound which is greater or smaller than an amount detected in the absence of the test compound indicates that the test compound is capable of regulating protease activity.

28. The method of item 24 wherein the polypeptide is produced in a host cell.

What is claimed is:

1. A method for screening a compound for its ability to regulate protease activity comprising the steps of:

incubating, in the presence and absence of a test compound:

a protease; and a polypeptide, wherein the polypeptide comprises (a) an anchor region, (b) a protease recognition site which comprises a protease cleavable peptide bond and at least 3 naturally adjacent amino acids on each side of the cleavable peptide bond, and (c) a detectable signal region, wherein the anchor region is bound to a solid support; and detecting the signal region bound to the solid support, wherein detecting an amount of the signal region bound to the solid support in the presence of the test compound which is greater or smaller than an amount detected in the absence of the test compound indicates that the test compound can regulate protease activity.

2. The method of claim 1 wherein the anchor region specifically binds to an antibody.

3. The method of claim 2 wherein the anchor region comprises protein A.

4. The method of claim 1 wherein the protease recognition site is a hepatitis C virus protease recognition site.

5. The method of claim 4 wherein the hepatitis C virus protease recognition site is selected from the group consisting of 4A/4B, 4B/5A, 5A/5B, and serial combinations thereof.

6. The method of claim 1 wherein the detectable signal region comprises an epitope.

7. The method of claim 6 wherein the epitope comprises the amino acid sequence FLAG (SEQ ID NO:1).

8. The method of claim 1 wherein the polypeptide further comprises a linker region between the anchor region and the protease recognition site.

9. The method of claim 1 wherein the anchor region specifically binds to an antibody, the protease recognition site is a hepatitis C virus protease recognition site which is selected from the group consisting of 4A/4B, 4B5A, 5A/5B, and serial combinations thereof, and the signal region comprises an epitope.

10. The method of claim 9 wherein the anchor region comprises protein A and the epitope comprises the amino acid sequence FLAG (SEQ ID NO:1).

11. The method of claim 10 further comprising a linker region between the anchor region and the protease recognition site.

* * * * *